United States Patent
Mainar López et al.

(10) Patent No.: US 9,746,418 B2
(45) Date of Patent: Aug. 29, 2017

(54) PORTABLE REFLECTOMETER AND METHOD FOR CHARACTERISING THE MIRRORS OF SOLAR THERMAL POWER PLANTS

(75) Inventors: Marta Mainar López, Saragossa (ES); David Izquierdo Núñez, Saragossa (ES); Iñigo Salinas Áriz, Saragossa (ES); Carlos Heras Vila, Saragossa (ES); Rafael Alonso Esteban, Saragossa (ES); Francisco Villuendas Yuste, Saragossa (ES); Ana Margarita Lopéz de Lama, legal representative, Saragossa (ES); Javier Asensio Pérez-Ullivarri, Saragossa (ES)

(73) Assignee: Abengoa Solar New Technologies, S.A., Seville (ES)

( * ) Notice: Subject to any disclaimer, the term of this patent is extended or adjusted under 35 U.S.C. 154(b) by 29 days.

(21) Appl. No.: 13/810,692

(22) PCT Filed: Jul. 20, 2011

(86) PCT No.: PCT/ES2011/000234
§ 371 (c)(1),
(2), (4) Date: Mar. 21, 2013

(87) PCT Pub. No.: WO2012/010724
PCT Pub. Date: Jan. 26, 2012

(65) Prior Publication Data
US 2013/0169950 A1 Jul. 4, 2013

(30) Foreign Application Priority Data
Jul. 21, 2010 (ES) .................................. 201000942

(51) Int. Cl.
*G01N 21/47* (2006.01)
*G01N 21/55* (2014.01)
*G01M 11/00* (2006.01)

(52) U.S. Cl.
CPC ........... *G01N 21/55* (2013.01); *G01M 11/005* (2013.01); *G01N 21/47* (2013.01);
(Continued)

(58) Field of Classification Search
CPC ...... G01N 21/55; G01N 21/47; G01M 11/005
(Continued)

(56) References Cited

U.S. PATENT DOCUMENTS 3,483,385 A 12/1969 Heaslip et al.
3,862,804 A 1/1975 Hoffmann
(Continued)

OTHER PUBLICATIONS

Brogren M et al.: "Analysis of the effects of outdoor and accelerated ageing on the optical properties of reflector materials for solar energy applications", Solar Energy Materials and Solar Cells, Elsevier Science Publishers, vol. 82, No. 4, May 30, 2004 (May 30, 2004), pp. 491-515, Amsterdam, NL.
(Continued)

*Primary Examiner* — Kara E Geisel
*Assistant Examiner* — Hina F Ayub
(74) *Attorney, Agent, or Firm* — Kilpatrick Townsend & Stockton LLP

(57) ABSTRACT

The invention relates to a portable reflectometer and to a method for characterizing the collector mirrors used in solar power plants for the in-field characterization of reflection coefficients. The equipment includes all of the components required for this measurement, such as a module to measure the reflection coefficient of the mirror, an electronic data acquisition and processing system, a system for processing data and controlling the equipment, a system for storing the
(Continued)

data of interest, a user interface system, and a system allowing communication between the aforementioned systems and an outer casing. The equipment can be used to characterize the specular reflection coefficient of flat or curved mirrors of different thicknesses, without requiring adjustments to be made to the equipment, minimizing the influence of diffuse reflection on the measurement.

26 Claims, 4 Drawing Sheets

(52) U.S. Cl.
CPC ............... *G01N 2201/0221* (2013.01); *G01N 2201/0625* (2013.01); *G01N 2201/0627* (2013.01)

(58) Field of Classification Search
USPC .................................................. 356/445–448
See application file for complete search history.

(56) References Cited

U.S. PATENT DOCUMENTS

| | | | |
|---|---|---|---|
| 3,971,951 A * | 7/1976 | Rikukawa et al. | 250/458.1 |
| 4,072,426 A * | 2/1978 | Horn | G01N 21/57 356/446 |
| 4,124,803 A * | 11/1978 | Bowers | G01N 21/57 250/341.7 |
| 4,687,329 A | 8/1987 | Schultz | |
| 4,877,954 A * | 10/1989 | Neuman | G06M 7/00 250/222.2 |
| 4,952,058 A * | 8/1990 | Noguchi | G01N 21/94 356/237.5 |
| 5,101,485 A * | 3/1992 | Perazzoli, Jr. | G06F 12/121 711/206 |
| 5,196,906 A | 3/1993 | Stover et al. | |
| 5,249,470 A * | 10/1993 | Hadley | B64C 27/008 73/655 |
| 5,260,584 A | 11/1993 | Popson et al. | |
| 5,361,769 A * | 11/1994 | Nilsson | 600/479 |
| 5,596,403 A * | 1/1997 | Schiff | G01B 11/26 356/139.03 |
| 5,659,397 A | 8/1997 | Miller et al. | |
| 5,696,863 A * | 12/1997 | Kleinerman | 385/123 |
| 5,751,424 A * | 5/1998 | Bostater, Jr. | G01N 21/8507 356/342 |
| 5,815,254 A | 9/1998 | Greene | |
| 7,042,580 B1 * | 5/2006 | Stanke | B24B 37/042 356/237.2 |
| 7,329,857 B1 * | 2/2008 | Weiss | G01F 23/2925 250/227.11 |
| 2002/0071124 A1 * | 6/2002 | Schwarz | G01J 3/02 356/445 |
| 2002/0144956 A1 * | 10/2002 | Silverstone et al. | 210/748 |
| 2002/0153473 A1 * | 10/2002 | Kurata | G01D 5/342 250/208.1 |
| 2002/0171841 A1 * | 11/2002 | Elkind | G01N 21/553 356/445 |
| 2002/0198799 A1 * | 12/2002 | Burden | G06Q 20/18 705/35 |
| 2003/0016353 A1 * | 1/2003 | Detalle et al. | 356/318 |
| 2004/0051862 A1 * | 3/2004 | Alcock | G01N 21/474 356/71 |
| 2004/0248059 A1 * | 12/2004 | Katsuda | A61C 19/004 433/29 |
| 2005/0151974 A1 * | 7/2005 | Butterfield | H04N 1/00058 356/448 |
| 2006/0023202 A1 * | 2/2006 | Delacour | G01N 21/55 356/121 |
| 2006/0152729 A1 * | 7/2006 | Drennen et al. | 356/432 |
| 2006/0192963 A1 * | 8/2006 | Frick | 356/420 |
| 2006/0206215 A1 * | 9/2006 | Clausen | A61B 5/1038 623/24 |
| 2006/0279732 A1 * | 12/2006 | Wang | G01J 3/02 356/326 |
| 2007/0145236 A1 * | 6/2007 | Kiesel | G01J 1/4228 250/208.1 |
| 2007/0268481 A1 * | 11/2007 | Raskar et al. | 356/218 |
| 2008/0034602 A1 * | 2/2008 | Schwarz | G01B 11/306 33/701 |
| 2008/0103714 A1 * | 5/2008 | Aldrich et al. | 702/81 |
| 2008/0120042 A1 * | 5/2008 | Richardson | G01N 21/8483 702/24 |
| 2008/0144004 A1 | 6/2008 | Rosenthal | |
| 2008/0288182 A1 * | 11/2008 | Cline | G01J 3/02 702/24 |
| 2009/0004464 A1 | 1/2009 | Diehl et al. | |
| 2009/0019713 A1 * | 1/2009 | Sullivan | A43D 1/025 33/3 A |
| 2009/0294702 A1 * | 12/2009 | Imanishi et al. | 250/576 |
| 2010/0002237 A1 | 1/2010 | Zalusky | |
| 2010/0033720 A1 * | 2/2010 | Van Neste | G01N 21/1702 356/337 |
| 2010/0141949 A1 * | 6/2010 | Bugge | 356/402 |
| 2010/0263709 A1 * | 10/2010 | Norman | F24J 2/07 136/246 |
| 2011/0047867 A1 * | 3/2011 | Holland | 47/1.5 |
| 2011/0120554 A1 * | 5/2011 | Chhajed | C09D 1/00 136/259 |
| 2012/0019819 A1 * | 1/2012 | Messerchmidt | 356/301 |
| 2012/0154814 A1 * | 6/2012 | Zare et al. | 356/445 |
| 2012/0321759 A1 * | 12/2012 | Marinkovich | A61B 5/0531 426/231 |
| 2013/0111490 A1 * | 5/2013 | Baruch | G06F 9/5005 718/104 |
| 2013/0208264 A1 * | 8/2013 | Ahadian | G01M 11/3145 356/73.1 |

OTHER PUBLICATIONS

C E Kennedy et al.: "Optical Durability of Candidate Solar Reflectors", Journal of Solar Energy Engineering, vol. 127, Jan. 1, 2005 (Jan. 1, 2005), pp. 262-269.
Dowden S et al.: "Reflectometer for fast measurements of mirror reflectivity", Measurement Science and Technology, IOP, vol. 8 No. 11, Nov. 1, 1997 (Nov. 1, 1997), pp. 1258-1261, Bristol, GB.
Pettit et al.: "Characterization of the reflected beam, profile of solar mirror materials", Solar Energy, Pergamon Press, vol. 19, No. 6, Jan. 1, 1977 (Jan. 1, 1977), pp. 733-741, Oxford, GB.
Polato P et al.: "Reflectance measurements on second-surface solar mirrors using commercial spectrophotometer accessories", Solar Energy, Pergamon Press, vol. 41, No. 5, Jan. 1, 1988 (Jan. 1, 1988), pp. 443-452, Oxford, GB.
Supplementary Search Report dated Jan. 31, 2014 for EP Application No. 11809308, filed Jul. 20, 2013. 3 pages.

* cited by examiner

PORTABLE REFLECTOMETER AND METHOD FOR CHARACTERISING THE MIRRORS OF SOLAR THERMAL POWER PLANTS

CROSS-REFERENCE TO RELATED APPLICATIONS

This application is a U.S. National Stage of PCT International Application No. PCT/ES2011/00234, filed on Jul. 20, 2011, entitled "Portable Reflectometer And Method For Characterising The Mirrors Of Solar Thermal Power Plants."

TECHNICAL FIELD OF THE INVENT ON

The present invention falls within the technology of optical measuring equipment or instruments.

More specifically, it relates to portable equipment for spectral characterization and in the field of coefficients of reflection of flat mirrors or with a certain degree of curvature, whether these are heliostat mirrors, Stirling, Fresnel . . . etc., all of these used in collectors for obtaining solar thermal energy. This equipment includes all the components needed to take this measurement, including data processing and sending them to a computer for storage.

BACKGROUND OF THE INVENTION

Within renewable energy, the collection of solar thermal technology can be found, which is of a technologically and economically importance in the domestic and industrial sector. Solar thermal energy produces electricity with a conventional thermoelectric cycle that requires heating a fluid at high temperature. These systems require the maximization of the concentration of solar energy at the point or points of absorption thereof, by using mirrors that can be completely flat, with a certain degree of spherical curvature, parabolic or cylinder-parabolic, depending on the technology of the solar thermal power plants.

Consequently, the value of the coefficient of reflectivity of the mirrors installed in these systems plays an important role in the performance of power plants that generate solar thermal energy. Furthermore, knowledge of these reflectivity values allows, together with information on environmental conditions of the area and other technical data of the plants, to forecast the power that will be generated in the near future in order for firms to properly manage energy resources.

For the operation and maintenance of electric energy production facilities, due to the large number of mirrors installed, it is convenient to have equipment that allows the characterization of reflectivity of each mirror quickly, conveniently and easily. The equipment that carries out a measurement of this type is called a reflectometer.

Given the optical characteristics of the solar energy absorbing elements which are included in these plants (maximum energy absorption and minimum energy losses, which determine dependencies of the optical parameters with the wavelength), the equipment must provide measurements of the mirrors according to the wavelength.

Similarly, the equipment must provide precise measurement of reflection value extremes close to the unit, generally in unfavorable environmental conditions, since the ambient light intensity will usually be high and even exceed in some cases, the signal to be measured itself. In addition, the requirement of high precision of the measurements is essential in solar thermal technology to maintain the efficiency in plants that produce electricity.

On the other hand, the reflection in the mirrors can be of two characters; diffuse and specular. Diffuse reflection is omnidirectional, unlike specular reflection in which the beam is reflected at a reflection angle equal to the angle of incidence. Due to the dirt that is deposited on the surface of the mirrors of the plant, the reflection of sunlight will have diffuse and specular components, specular reflection being useful only from the viewpoint of power generation, since it is the only one that will concentrate on the absorber element. Therefore, the equipment should minimize the contribution of diffuse reflection on the measurement of the reflection coefficient of the mirrors.

Finally, the equipment must be able to correctly measure the set of types of mirrors commonly used in the power plants. Specifically, it must be able to correctly measure flat mirrors, mirrors with a certain degree of spherical curvature, parabolic and cylinder-parabolic mirrors of different thicknesses without equipment adjustments.

A conventional reflectometer uses a broad spectrum light source and a variable filtering element that allows for sequentially select different wavelengths, such as a movable diffraction grating followed by a narrow slit. This option allows for varying the wavelength in a virtually continuous way, but in turn, results in a more complex and delicate system, with a low measurement dynamic range as the power of the input light that is achieved is very low. Furthermore, conventional equipment does not minimize the contribution of diffuse reflection, and in fact, in some cases it is of interest to collect all the scattered light and integrating spheres in detection are implemented.

The U.S. Pat. No. 5,815,254 describes a spectrophotometer device that can work in transmission measurement mode and reflection measurement mode. It uses a source of white light, halogen or Xe, optical fibers to carry the illumination light beam from the sample onto the sample surface, and a spectral analysis based on diffraction grating and a detector line.

The U.S. Pat. No. 3,862,804 describes double beam reflectometer equipment with switching mirror included in each measurement, the correction with the standard measurement, and integrating sphere to include in the measurement of scattered light reflection. The system uses white light, the monochromator for wavelength selection, illumination with collimated beams and integrating sphere in the detection which means that all the scattered light is collected and measured in the detection.

The U.S. Pat. No. 4,687,329 describes spectrophotometer equipment which uses a broad spectrum source, in this case ultraviolet, and various filters in fixed positions to perform a spectral measurement on a number of discrete points.

There is also a background of spectrophotometers in which a collection source of light sources of different wavelengths is used. In the patent US 2008/0144004 multiple light emitting diodes (LED) are used simultaneously to perform a transmission measurement for the detection of various analytes in blood. However, one true spectral measurement is not performed, but rather several simultaneous measurements at a few different wavelengths. Furthermore, there is no protection against ambient light nor is it possible to take measurements of reflection or reference.

None of the above equipment or other similar equipment meet the requirements necessary for measurement in the field of mirrors for solar collectors, either by range, sensitivity and/or mechanical configuration.

DESCRIPTION OF THE INVENTION

The present invention takes into account the specific characteristics of the problem mentioned above, to obtain portable, robust, and easy to use equipment, that takes measurements quickly, with an adequate sensitive and dynamic range, with sufficient tolerance in curvature and thickness of the mirror to be measured and that minimizes the contribution of the diffuse reflection in the measurement.

The equipment takes the measurement of the coefficient of specular reflection of mirrors at different wavelengths, these determined by light emitting diodes LED. The mirrors object of characterization may be flat or curved, and may be first or second side mirrors with different thicknesses.

Each wavelength constitutes a reflectance measurement optical channel in the equipment. For each reflectance measurement optical channel, the device performs two measurements, a reference measurement on a percentage of the light, emitted by the LED and a direct measurement of the light specularly reflected by the mirror. The equipment performs simultaneous measurement of reference and direct in each measurement optical channel to adequately correct the variations in the power of the LED emission of said channel.

The number of optical channels can be variable, with at least one and covering the desired spectral range with commercial LEDs in the ultraviolet range to near infrared. With the usual requirements for spectral characterization of a facility of solar thermal energy production, it may be sufficient to have about five measurement wavelengths.

For each optical channel, the angle of incidence of the light beam from the LED and the collection angle of the light beam reflected by the mirror is the same, to ensure measurement of specular reflection. The size of the illuminated area on the mirror determines the amount of scattered light that may be introduced on the reflectance measurement. To minimize this amount of undesired scattered light, the illuminated area on the mirror should be as small as possible. For this, the numerical output aperture of the illumination beam from the LED is limited, by a diaphragm with a certain diameter and length, placed at the output of the LED and oriented on the optical axis of the system to ensure the angle of incidence of the light beam required on the mirror.

The beam reflected by the mirror in specular reflection is collected by a lens which focuses the beam onto a detector for the direct measurement of the specularly reflected light by the mirror. This lens and detector system is oriented on the optical axis of the system to ensure the collection angle of the light beam in specular reflection. The size of the lens relative to the size of the beam at this point determines the tolerance of the system against the curvature of the mirror and against the position of the mirror surface with respect to the measuring equipment determined by the thickness of the glass that protects the mirror face. If the size of the lens is not larger than the size of the beam at that point, the conditions of curvature of the mirror or of the thickness of the mirror for the correct measurement, would be unique and variations thereof would mean that not all of the light beam specularly reflected by the mirror would be collected by the lens and reached the detector, leading to an error of reflectance measurement. In order to have sufficient tolerance in curvature and thicknesses of the mirrors typical in a solar energy production facility, a size of lens that is twice the size of the beam at that point may be sufficient.

The combination of the optical parameters of the numerical aperture of the illumination beam, lens size and focal length of the lens, determines the relative positions of the set of LED, mirror, lens and detector and hence the size of the equipment. In order to achieve manageable portable equipment, it is desirable that it has lenses with a focal maximum of 15 mm and maximum diameter of half an inch.

To obtain a measurement with high sensitivity, that allows accurately resolving values of the reflection coefficients very close to unit, it is necessary for the acquisition system to have a relation signal to noise ratio large enough. Since the optical signal is primarily from the environmental sunlight, that is, it is a high intensity signal, it is essential to perform some type of treatment to said signal that allows for the signal to noise ratio to be high. It is most appropriate in this case that the signal processing by implementing an extraction algorithm such as synchronous detection or lock-in. To perform a treatment of this type, it is necessary that the signal measurement can be easily distinguished from background noise, which is usually achieved by applying some type of modulation thereof.

Another essential feature in equipment of this type is the possibility of treatment and export of data in a convenient and flexible way, that they can be stored in the manner deemed most appropriate. This can be solved through wireless communication with a standard network protocol, by means of conventional cable connection type via USB port or also by using conventional computer memory sticks.

The general scheme of the measuring equipment is as follows:

Various light emitting diodes or LEDs, which cover the range of wavelengths in which the mirrors are desired to be characterized. In one preferred embodiment an LED would be used for each wavelength.

Two photodetectors for each LED used, one for the reference signal and another for obtaining the direct signal.

A circuit which performs the functions of modulation of the LED sources and the detection and processing of the signals of interest, which may be synchronous detection (lock-in), analog or digital, to extract the signal from the possible optical and environmental background noise.

A central system for the processing of information and control of equipment, which can be an external computer or system integrated in the equipment itself, such as a microcontroller. This system controls the overall operation of the system, selecting the electronic components correspondent to the channel used at all times and monitoring internal and external communications.

A system for storing the data of interest in the manner considered most suitable, which can be the memory of the computer itself or a removable memory stick in the case of an integrated, system.

A user interface system, including a screen and buttons needed for managing the equipment.

A system of communication between the system of detection and signal processing, the central system for processing data, the system for storage of the data and the user interface system.

A casing that provides adequate insulation of the electronic and optical components of the system, allowing for their easy transport and simple and repetitive attachment to the mirrors to be measured.

The software to be installed in the equipment, needed for carrying out communication with the same and subsequent processing of the acquired information, obtaining the coefficient values of reflection for each one of the wavelengths from the relationship between direct signal and signal of reference prior calibration standard. Likewise the software provides global values by weighting the reflectance values obtained with the corresponding weight of the wavelengths in the solar spectrum.

One of the advantages and advancements provided by the invention is the fact that the system is capable of performing measurements of reflectance of the mirrors with ambient light and in the field, without special darkness or protection conditions.

Another of the advantages and advancements provided by the invention is the fact that the system is able to characterize mirrors of different curvatures and different thicknesses with a high tolerance in these parameters without needing to make any adjustments in the equipment.

Another very important advancement is to minimize the contribution of reflected scattered light in the measurement, a point of great interest in measurements in plants where the dirt on the mirrors is relevant.

DESCRIPTION OF THE DRAWINGS

In order to aid a better understanding of the characteristics of the invention, attached to this specification is a series of figures where, in a purely indicative and not limiting manner, the following has been represented.

Figure 1A:
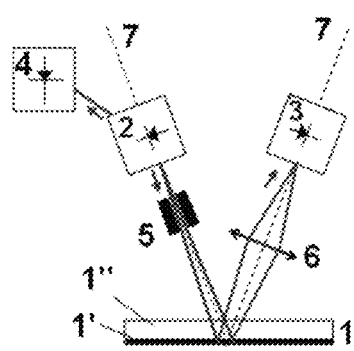
FIG. 1a represents a diagram of the optical system corresponding to a measurement wavelength, which includes the emitter, the two connected detectors and the collection lens of the reflected beam, with their spatial arrangement with respect to the mirror to be measured, in the first and second preferred embodiments.

With regard to the references used in the figures:
(1) Mirror to be characterized (1') mirrored surface (1''') glass of the mirror.
(2) LED beam emitter.
(3) Reflector detector.
(4) Reflection reference detector.
(5) Diaphragm that limits the beam size on the surface of the mirror.
(6) Lens that collects the beam reflected by the mirror.
(7) Line showing the optical axis of the system.
(8) Part containing the direct reflection measurement LED emitters and detectors,
(9) Lateral casing which also forms the support part for the equipment on the mirror.
(10) O-ring to ensure proper support of the equipment on the mirror without damaging its surface,
(11) Printed circuit board which houses the references measurement detectors,
(12) System for acquisition and processing of the signal
(13) Module for measuring the coefficient of the reflection of the mirror
(14) Data processing and equipment control system
(15) Data storage system
(16) Synchronous detection
(17) Analog-to-digital converter
(18) Modulation generator
(19) Transimpedance amplifier
(20) Control via digital outputs
(21) LED modulating signals
(22) Measured electric analog signals
(23) User interface
(24) Commands
(25) Data
(26) Equipment screen
(27) Buttons or keyboard of the equipment

DETAILED DESCRIPTION OF THE INVENTION

In order to achieve a better understanding of the invention, the following described a series of preferred embodiments of the claimed invention.

First Preferred Embodiment of the Invention

It proposes a preferred embodiment based on an optical system with the configuration shown in FIG. 1a for each optical channel.

The mirrors (1) for solar collectors are commonly second face mirrors, in such a way that on the mirror surface, there is a glass with a thickness of between approximately 3 mm and 5 mm. These mirrors may be flat, spherically curved in the case of power plants for solar concentration at a point, or cylinder-parabolic, as in the case of solar concentration on core tubes. The mirror must have a very high reflection coefficient in the solar spectrum.

The reflection measurement is obtained from measurements performed by the reflection detector (3) after the beam generated by the LED emitter (2) passes through the outer glass (1"), is reflected on the mirror surface specularly (1') and passes through the outer glass (1") again.

The LED (light emitting diode) (2) is oriented on the optical axis (7) of the system with a defined angle of incidence on the mirror (1), so that it coincides with the direction of the maximum emission of the LED with the orientation of the mirrored surface. In this preferred embodiment the angle of incidence is 15°. This LED output beam in the direction of the mirror is limited in numerical aperture by a diaphragm (5) to ensure the beam size on the mirror surface. Furthermore, the system obtains a reference signal from the measurement of part of the light emitted by the LED in a different direction by means of the detector (4).

The specular reflection of the beam on the mirror is collected by the lens (6) of double the size of the beam size at this point. This lens (6) is oriented according to the optical axis of the system, and focuses the light beam on the direct light measuring detector (3).

Figure 2:
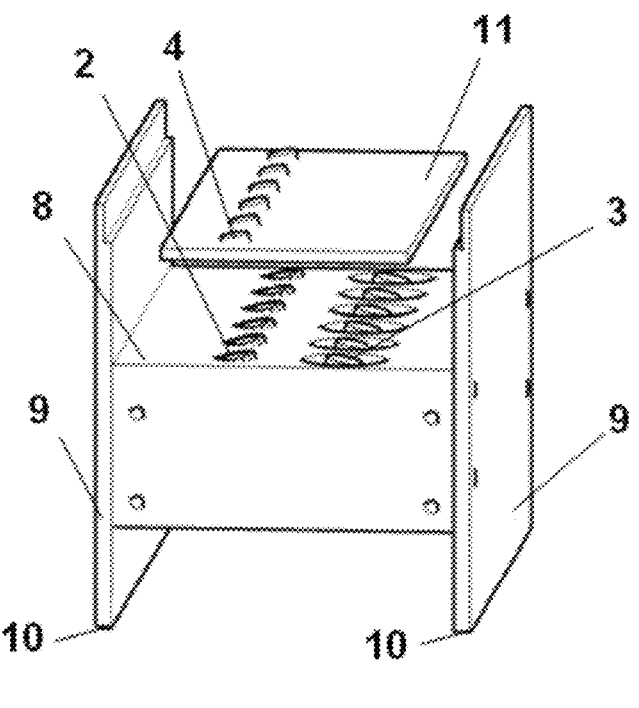
FIG. 2 represents the top view of the mechanical casing where the optoelectronic components of the system are placed according to a line system configuration, in the first and third preferred embodiments.
Figure 3:
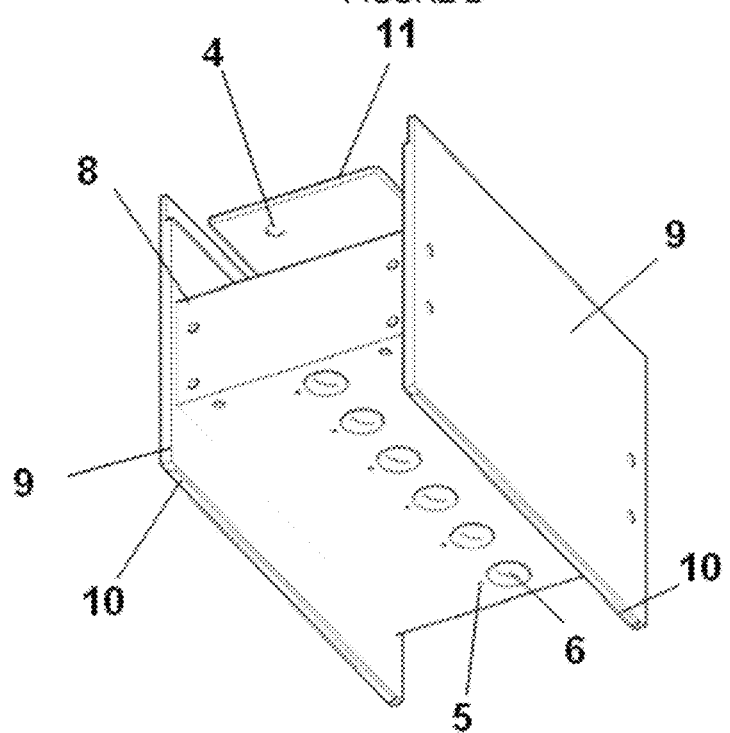
FIG. 3 represents the bottom view of the mechanical casing, in the first and third preferred embodiments.

FIGS. 2 and 3 show the mechanical aspect of the embodiment, not including the upper and front casing that protect the components. Included in the figures are the two lateral casings (9) which form, in this embodiment, the support pieces for the equipment on the mirror and allow repetitive positioning at the height of optical system on the mirror to be characterized (1) in a simple and fast way. The piece (8) that contains the emitters, detectors, diaphragms and lenses for measuring the reflection can also be distinguished.

In this first preferred embodiment the arrangement of the reflectance optical channels for reflectance measurement is in a line. The emitters (2) and direct light detectors (3) are placed on the upper face of the piece (8). On the underside, the lenses (6) and diaphragms (5) are placed which, in this embodiment, are holes made on the same piece that connects to the LED position. The rubber O-rings (10) placed along the lower profile of the support pieces (9) ensure the correct support of the equipment on the mirror without damaging it. The reference detectors (4) are placed on the LED emitters (2) for measuring the light beam emitted by them in that direction, and are supported on the same printed circuit board (11) containing the electronics of the equipment.

Figure 6:
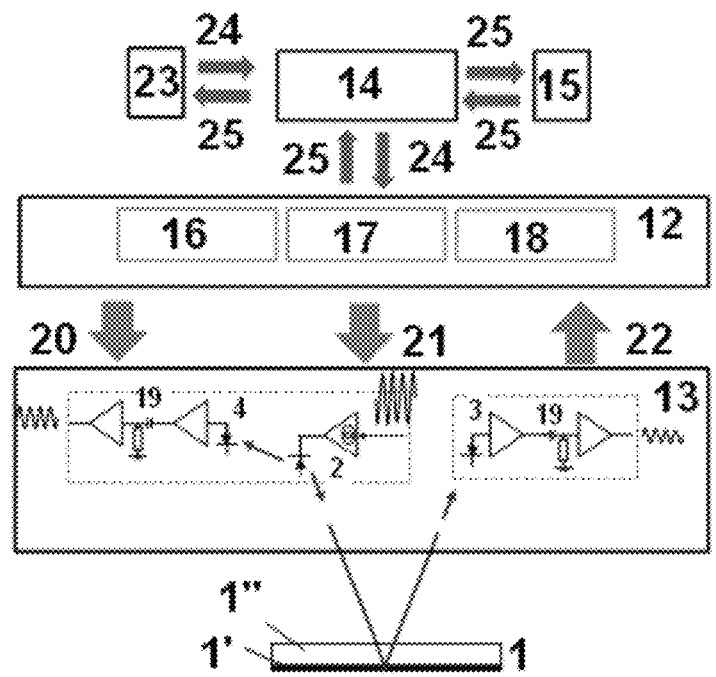
FIG. 6 represents the full diagram of the proposed embodiments, including the optical system and the electronic components, as well as the data acquisition card that performs the functions of analog-to-digital conversion of the signals and the communication with the PC.
Figure 7:
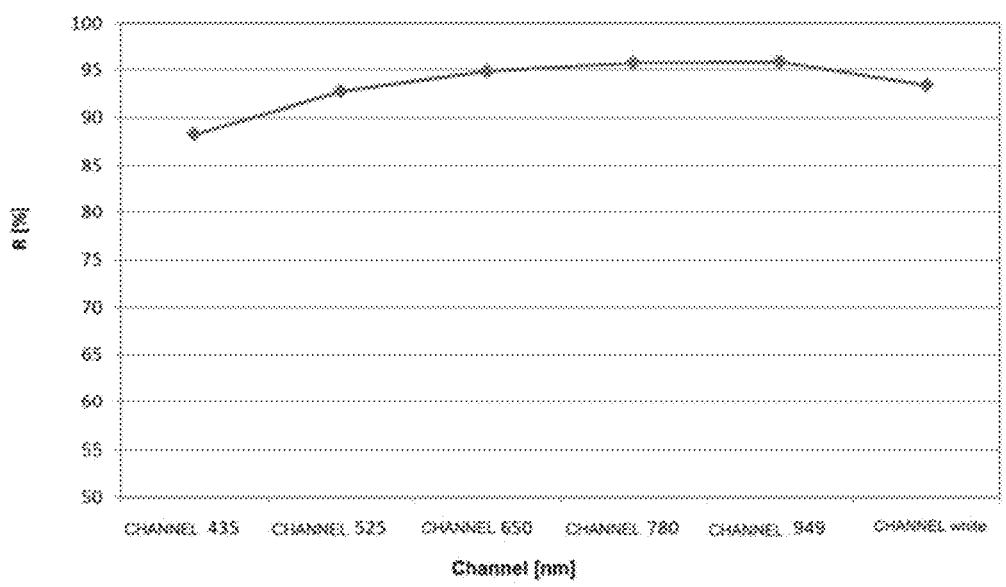
FIG. 7 represents the specific example of a measurement of a flat mirror.

FIG. 6 shows the complete diagram including the system for data acquisition and processing (12), the data processing system and equipment control (14), the data storage system (15) and the interface user system (23). In order for the measurement to be taken without influence of the ambient light, the data acquisition and processing system (12) consists of a signal (21) of the emitters which is modulated, by sinusoidally varying the power supply current of the LEDs (each of them in a different time). This modulation allows for extracting the signal of interest in the detectors (3, 4), filtering out all frequency components except for that corresponding to the LED being measured at each moment. The modulation signals of the LEDs (21) are generated in the modulation generator (18) by a local oscillator.

In the preferred embodiment 5 LED's have been chosen at wavelengths of 435, 525, 650, 780, 949 that cover the spectral region of interest plus an LED that emits white light for a faster integrated measurement of the visible spectrum.

The photodetectors (3, 4) are followed by two amplification stages (19) whose gain depends on the value of the resistances they have. One of these resistances may be a digital potentiometer whose value can be controlled via software, allowing for the adjustment of the gain of each channel at any time using the digital outputs (20) of the analog-to-digital conversion system (17).

The frequency filtering is carried out by synchronous detection (lock-in) in the signal detection and processing system (12). The synchronous detection system involves amplification of the signal exclusively to the modulation frequency, whose frequency is obtained from an electrical reference signal. The synchronous detection can be analog or digital.

In the case of synchronous analog detection, the signals detected in the photodetectors (3,4) are processed in a lock-in amplifying analog circuit, whose output (a continuous signal) is directed to the analog-to-digital converter (17). The analog-to-digital conversion is performed with a data acquisition board DAQ which also responsible for the control via digital outputs (20) of the power supply of the boards of the emitters (2) and detectors (3, 4), as well as of the selection of the optical channel to be measured at each time.

In the case of synchronous digital detection, the first step is the digitization of the modulation signals (21) and those from the photodetectors (3, 4) by means of the DAQ for subsequent introduction into a digital processing system of the signal, such as a DSP (digital signal processor), an FPGA (Field Programmable Gate Array), a microcontroller capable of digital signal processing, or a computer that performs synchronous detection algorithm.

The detection and signal processing system (12) communicates with the data processing and equipment control system (14) which can be a conventional external computer.

Another possibility is to replace the control computer by a system built into the actual equipment, such as a microcontroller, which can also be used to replace the analog-to-digital converter (17). In the case of performing the processing in digital form, the same element used to perform the synchronous processing (FPGA, DSP, microcontroller capable of digital signal processing) can replace both the DAQ and the control computer (14). In the latter case, the processor element can also replace the local oscillator used in the modulation generator (18), which eliminates the need to acquire the modulation signal (21), as it is generated by the same processing system.

Figure 5:
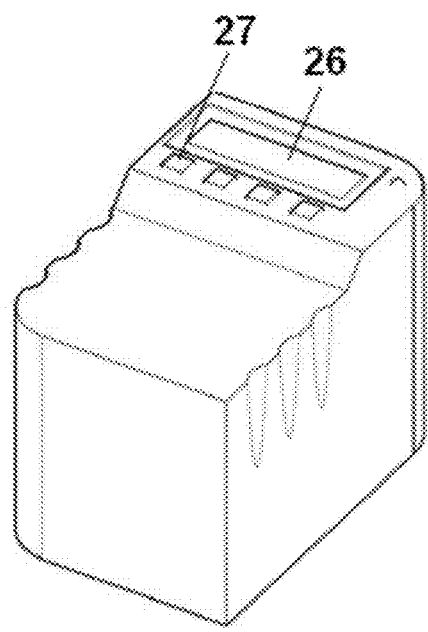
FIG. 5 represents the external view of the equipment according to the first and third preferred embodiments.

FIG. 5 shows the external appearance of the equipment in an embodiment with all the systems built into the equipment.

A program installed on the data processing equipment control system, allows for the use of commands (24) which programmed into the signal detection and processing system (12) to perform all the necessary functions in the measurement process, including the measurement channel selection for the corresponding LED modulation and reading the data (25) obtained for further processing and storage. It also enables the storage of relevant data in the storage system (15) and management of the data and commands with the user interface system (23). A specific example of measurement corresponding to a flat mirror is shown in FIG. 5.

The equipment operation method comprises the following steps for obtaining the reflection and transmission coefficients of the tubes:

1. Position the equipment in a way in which it is stably supported on the mirror.
2. Turn on the equipment emitters.
3. In a consecutive way, each one of the LED emitters is modulated to the measurement frequency.
4. This output LED emitter beam in the direction of the mirror is limited in numerical aperture by a diaphragm (5) in order to ensure the size of the beam on the mirror surface.
5. The beam generated by the LED emitter (2) is specularly reflected in the mirror surface.
6. The specular reflection of the beam on the mirror is collected by the lens (6) of double the size of the beam at this point. This lens (6) is oriented according to the optical axis of the system, and focuses the light beam on the direct light measurement detector (3).
7. On the other hand, the system obtains a reference signal from the measurement of the part of light emitted by the LED in the other different direction, by means of the detector (4).
8. The data obtained in the reflection detector corresponding to the modulated LED is normalized with its reference signal, in order to eliminate the influence of variations in the intensity of emission of each LED.
9. Subsequently, the coefficient of the reflection of the mirror for each wavelength is obtained. This final value of the coefficient is obtained also by a known standard reference.

10. The values corresponding to the standard are stored in the equipment after a prior calibration, which requires the use of a mirror with known reflection coefficients. This calibration is performed following the first eight steps of this very procedure.
11. Subsequent processing of the acquired information, basically consisting in obtaining the values of the reflection coefficient for each of the wavelengths from the relation between the direct signal and the reference signal prior to calibration using standard.
12. Obtaining the overall values of reflectance by weighting the values obtained in each wavelength with the weight corresponding to said wavelength in the solar spectrum.

Second Preferred Embodiment of the Invention

Figure 4:
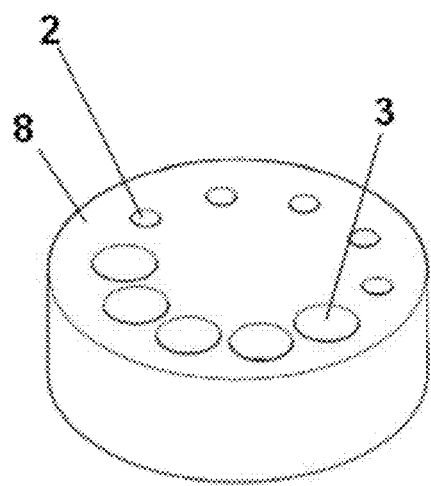
FIG. 4 represents the top view of the mechanical casing where the optoelectronic components are placed according to a circle configuration system, in the second and fourth preferred embodiments, in the second and fourth preferred embodiments.

A second preferred embodiment is proposed, which is identical to the first preferred embodiment except for the arrangement of the optical channels which is in a circle instead of being in line as shown in FIG. 4. Thus, the illumination point on the mirror surface is the same for all the LED diodes and the reflectance measurement of each channel corresponds to the same point on the mirror.

Third Preferred Embodiment of the Invention

Figure 1B:
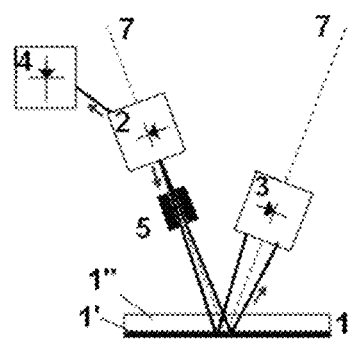
FIG. 1b represents a diagram of the optical system corresponding to a measurement wavelength, which includes the emitter and two connected detectors with their spatial arrangement with respect to the mirror to be measured, in the third and fourth preferred embodiments.

A third preferred embodiment is proposed, which is identical to the first preferred embodiment except that the lens is removed in each measurement channel and in its place, the detector is directly placed as shown in FIG. 1 b. Thus, the specular reflection of the beam on the mirror leads directly to the direct light measuring detector (3).

Fourth Preferred Embodiment of the Invention

A fourth preferred embodiment is proposed, which is identical to the second preferred embodiment except that the lens is removed in each measurement channel and in its place, the detector is directly placed as shown in FIG. 1 b. Thus, the specular reflection in the mirror of the beam leads to the direct light measuring detector (3).

Although the main application of this invention is the use of the equipment for the control in situ of the optical characteristics of flat and cylinder-parabolic mirrors of solar thermal power plants, its extension to other industrial fields that require measurement equipment similar characteristics is not ruled out.

The invention claimed is:

1. A portable reflectometer for the spectral measurement of the specular reflection of mirrors of solar collectors, the portable reflectometer comprising:
   a module that carries out the measurement of the coefficient of the reflection of the mirror with at least a plurality of light emitting diodes as optical sources and a plurality of reflection photodetectors, one reflection photodetector respectively for each of the plurality of light emitting diodes;
   a respective diaphragm for each of the plurality of light emitting diodes, each respective diaphragm having a diameter and a length larger than an aperture of the diaphragm, wherein each diaphragm limits, in size and aperture, the output light beam of the respective light emitting diode that is incident on the mirror, to ensure the size of the area illuminated on the mirror surface, thus limiting the contribution of diffuse reflection in the measurement, and wherein each of the plurality of reflection photodetectors is positioned to receive the respective output light beam after the output light beam has specularly reflected from the mirror;
   an electronic system for acquiring and processing signals comprising a synchronous, analogical or digital detection, an analog-to-digital converter, an electronic modulation generator or a microprocessor configured to modulate the emission of light by each of the plurality of light emitting diodes to a respective measurement frequency, and a digital or analog electronic filter that filters the signals received from the respective reflection photodetectors to filter out frequency components except for the respective measurement frequency, the electronic system obtaining values for the reflectance of the mirror at specific light wavelengths;
   a data processing and equipment control system that provides global reflectance values by weighting the obtained values with weights according to their respective wavelengths in the solar spectrum;
   a system for storing relevant data;
   a user interface system;
   a system for the communication between the above systems; and
   an exterior casing.

2. The portable reflectometer according to claim 1 wherein the photodetectors are followed by two amplification steps.

3. The portable reflectometer according to claim 2 wherein at least one of the two amplification steps has a gain that can be varied at any moment via software commands.

4. The portable reflectometer according to claim 1 wherein the number of light emitting diodes is between 2 and 24 within the spectral range between 300 and 2500 nm corresponding to the solar spectrum.

5. The portable reflectometer according to claim 4 wherein 5 LEDs are installed at wavelengths 435, 525, 650, 780 and 949 nm, plus a LED that emits white light.

6. The portable reflectometer according to claim 1 wherein the arrangement of the plurality of light emitting diodes is such that they are placed in a linear configuration.

7. The portable reflectometer according to claim 1 wherein the arrangement of the plurality of light emitting diodes is such that they are placed in a circular configuration such that beams from more than one of the light emitting diodes are directed to the same point of the mirror.

8. The portable reflectometer according to claim 1 wherein each of the plurality of light emitting diodes is oriented in such a way that the maximum emission direction of the light beam coincides with the optical axis of incidence of the beam on the mirror.

9. The portable reflectometer according to claim 1, further comprising a plurality of lenses, one lens respectively for each of the plurality of light emitting diodes, wherein each respective lens and reflection photodetector are oriented according to the optical axis of the system defined by the specular reflection and each of the plurality of lenses is larger in size than the beam emitted by its respective light emitting diode and focuses the light beam on its respective reflection photodetector.

10. The portable reflectometer according to claim 9 wherein the size of each of the plurality of lenses is double the size of the respective beam upon entry into the lens.

11. The portable reflectometer according to claim 10 wherein each of the plurality of lenses has a focal maximum of 15 mm and a maximum diameter of 12.7 mm (half an inch), which enables achieving manageable portable equipment.

12. The portable reflectometer according to claim 9, wherein each of the plurality of lenses is sufficiently larger than its respective specularly-reflected beam such that all of the specularly-reflected beam is collected by the lens when the portable reflectometer is used to characterize flat second face mirrors having protective glass layers between 3 and 5 millimeters thick.

13. The portable reflectometer according to claim 1 wherein the modulation generator is a local oscillator.

14. The portable reflectometer according to claim 1 wherein the analog-to-digital conversion is performed with a data acquisition board DAQ or with a microcontroller.

15. The portable reflectometer according to claim 1 wherein the digital processing system used in the synchronous detection and in the modulation generator are the same.

16. The portable reflectometer according to claim 1 wherein the data processing and equipment control system is a computer external to the portable reflectometer.

17. The portable reflectometer according to claim 16 wherein the storage system of relevant data is located in the computer external to the portable reflectometer.

18. The portable reflectometer according to claim 16 wherein the user interface system is located in the computer external to the portable reflectometer.

19. The portable reflectometer according to claim 1 wherein the data processing and equipment control system is a system built into the portable reflectometer itself.

20. The portable reflectometer according to claim 19 wherein the system built into the portable reflectometer itself replaces at least one of the components used also in the system processes for detection and processing of the signal, these components being the synchronous detector, the analog-to-digital converter and the modulation generator, as well as those of the storage system and those of the user interface system.

21. The portable reflectometer according to claim 19 wherein the system built into the equipment itself replaces the storage system and/or the user interface system carrying out their functions.

22. The portable reflectometer according to claim 1 wherein the plurality of light emitting diodes are arranged in a line and the plurality of reflection photodetectors are arranged in a corresponding line; wherein the plurality of light emitting diodes and the plurality of reflection photodetectors are placed on the upper side of a piece, and on the lower face are placed the diaphragms, which, in this embodiment, are holes made on the same piece that connects to the LED position; wherein rubber O-rings are placed along the lower profile of pieces forming a casing of the portable reflectometer to ensure the correct support of the portable reflectometer on the mirror without damaging it; and wherein reference detectors are placed on the plurality of light emitting diodes for measuring the light beam emitted by them in that direction, and are supported on the same printed circuit board containing the electronics of the equipment.

23. A portable reflectometer for measuring the spectral reflection of a mirror, the portable reflectometer comprising:
a plurality of light emitting diodes emitting light at different respective wavelengths, each of the plurality of light emitting diodes being directed toward the mirror at a respective angle of incidence with the mirror;
a modulator that modulates each of the plurality of light emitting diodes to emit light modulated at a respective measurement frequency;
a plurality of diaphragms each having a diameter and a length larger than an aperture of the diaphragm, one diaphragm respectively for each of the light emitting diodes, wherein each plurality of diaphragms limits the size of the beam that reaches the mirror from the respective light emitting diode;
a plurality of reflection photodetectors, one reflection photodetector respectively for each of the plurality of light emitting diodes, each of the plurality of reflection photodetectors positioned to receive light from the respective light emitting diode after the light has specularly reflected from the mirror, each of the plurality of reflection photodetectors producing an electronic signal indicative of the intensity of light falling on the respective reflection photodetector;
a digital or analog electronic filter that filters out frequencies other than the measurement frequency from the signal produced by the particular one of the plurality of reflection photodetectors being measured at each moment; and
an electronic system that receives the signals produced by the plurality of reflection photodetectors and determines a global reflectance value for the mirror from a weighted average of the signals from the photodetectors.

24. A method of measuring the coefficient of reflection of a mirror for a solar thermal power plant, the method comprising:
providing a measurement module that comprises a plurality of light emitting diodes configured to emit light at different respective wavelengths; a plurality of diaphragms, one diaphragm respectively for each of the plurality of light emitting diodes, wherein each of the plurality of diaphragms is sized and positioned to limit the size of the beam produced by the respective light emitting diode; a plurality of reflection photodetectors, one reflection photodetector respectively for each of the plurality of light emitting diodes, each of the plurality of reflection photodetectors positioned to receive light from the respective light emitting diode after the light has specularly reflected from the mirror; a modulator configured to modulate the intensity of the light produced by each of the plurality of light emitting diodes; and a digital or analog filter configured to filter out frequencies from signals produced by the plurality of reflection photodetectors;
energizing each of the plurality of light emitting diodes to produce a respective beam from each of the plurality of light emitting diodes;
limiting the size of each of the beams using the respective diaphragm having a diameter and a length larger than an aperture of the diaphragm;
modulating the intensity of each respective beam at the respective measurement frequency by the modulator;
passing each respective beam through the glass of a second face mirror to reflect from the second face of the mirror;
receiving the respective beam by the respective reflection photodetector after the beam has reflected from the mirror;
producing, by the respective reflection photodetector, a signal indicative of the intensity of light falling on the respective reflection photodetector;
filtering, using the analog or digital electronic filter, the signal produced by each respective reflection photodetector to remove frequencies other than the respective measurement frequency; and obtaining a value of the reflection coefficient for each of the wavelengths based on the filtered signal amplitude.

25. The method of claim 24, wherein the measurement module further comprises a plurality of reference photodetectors, one reference photodetector respectively for each of the plurality of light emitting diodes, the method further comprising:
   directing a portion of the light emitted by each of the plurality of light emitting diodes directly to its respective reference photodetector;
   producing, by the respective reference photodetector, a signal indicating the intensity of light falling on each of the plurality of reference photodetectors; and
   normalizing the data obtained from each respective reflection photodetector using the signal produced by each respective reference photodetector;
   wherein receiving the respective beam by the respective reflection photodetector after the beam has reflected from the mirror comprises directly receiving the respective reflected beam by the respective reflection photodetector after the beam has reflected specularly from the mirror, without passing through any intervening lens.

26. The method of claim 24, wherein the measurement module further comprises a plurality of lenses, one lens respectively for each of the plurality of light emitting diodes, wherein each respective lens is positioned to receive the beam from the respective light emitting diode after the reflection of the beam from the mirror, and wherein each respective lens is larger in aperture than the respective reflected beam, the method further comprising:
   receiving the beam from each respective light emitting diode by the respective lens after the beam has reflected from the mirror; and
   directing, by the respective lens, the reflected beam to the respective reflection photodetector.

* * * * *